United States Patent
Yi et al.

(10) Patent No.: US 6,930,782 B1
(45) Date of Patent: Aug. 16, 2005

(54) END POINT DETECTION WITH IMAGING MATCHING IN SEMICONDUCTOR PROCESSING

(75) Inventors: Jingang Yi, Albany, CA (US); Cangshan Xu, Fremont, CA (US)

(73) Assignee: Lam Research Corporation, Fremont, CA (US)

( * ) Notice: Subject to any disclaimer, the term of this patent is extended or adjusted under 35 U.S.C. 154(b) by 33 days.

(21) Appl. No.: 10/401,446

(22) Filed: Mar. 28, 2003

(51) Int. Cl.$^7$ ................................. G01B 9/02
(52) U.S. Cl. ..................................... 356/504
(58) Field of Search ............... 356/504, 491, 356/492, 496, 499, 503

(56) References Cited

U.S. PATENT DOCUMENTS

| | | |
|---|---|---|
| 4,462,860 A | 7/1984 | Szmanda |
| 4,516,855 A | 5/1985 | Korth |
| 4,647,207 A | 3/1987 | Bjork et al. |
| 4,653,924 A | 3/1987 | Itonaga et al. |
| 4,681,450 A | 7/1987 | Azzam |
| 4,710,030 A | 12/1987 | Tauc et al. |
| 4,776,695 A | 10/1988 | van Pham et al. |
| 4,793,895 A | 12/1988 | Kaanta et al. |
| 4,844,617 A | 7/1989 | Kelderman et al. |
| 4,957,368 A | 9/1990 | Smith |
| 5,036,015 A | 7/1991 | Sandhu et al. |
| 5,042,951 A | 8/1991 | Gold et al. |
| 5,045,149 A * | 9/1991 | Nulty .......................... 438/16 |
| 5,061,072 A | 10/1991 | Folkard et al. |
| 5,067,805 A | 11/1991 | Corle et al. |
| 5,081,421 A | 1/1992 | Miller et al. |
| 5,081,796 A | 1/1992 | Schultz |
| 5,166,752 A | 11/1992 | Spanier et al. |
| 5,213,655 A | 5/1993 | Leach et al. |
| 5,240,552 A | 8/1993 | Yu et al. |
| 5,308,438 A | 5/1994 | Cote et al. |
| 5,321,304 A | 6/1994 | Rostoker |
| 5,337,015 A | 8/1994 | Lustig et al. |
| 5,337,150 A * | 8/1994 | Mumola ....................... 356/632 |
| 5,413,941 A | 5/1995 | Koos et al. |
| 5,433,651 A | 7/1995 | Lustig et al. |
| 5,439,551 A | 8/1995 | Meikle et al. |

(Continued)

FOREIGN PATENT DOCUMENTS

EP     0 663 265 A1     7/1995

(Continued)

OTHER PUBLICATIONS

W. H. Steel, "Interferometry,"*Cambridge University Press*, Second Edition 1983, New York, NY.

(Continued)

*Primary Examiner*—Gregory J. Toatley, Jr.
*Assistant Examiner*—Michael A. Lyons
(74) *Attorney, Agent, or Firm*—Brinks Hofer Gilson & Lione

(57) ABSTRACT

An end point detection system may compare a production image developed during processing of production semiconductor wafer with a reference image. The reference image is representative of a desired state of processing of the production semiconductor wafer. The reference image is determined by processing a reference semiconductor wafer. The reference semiconductor wafer may be part of a wafer group of similar wafers that includes the production semiconductor wafer. The end point detection system may dynamically develop the production image during processing of the production semiconductor wafer. Indication may be provided by the end point detection system when the reference image and the production image are substantially similar.

32 Claims, 8 Drawing Sheets

U.S. PATENT DOCUMENTS

| | | | |
|---|---|---|---|
| 5,486,701 | A | 1/1996 | Norton et al. |
| 5,517,312 | A | 5/1996 | Finarov |
| 5,595,526 | A | 1/1997 | Yau et al. |
| 5,597,442 | A | 1/1997 | Chen et al. |
| 5,609,511 | A | 3/1997 | Moriyama et al. |
| 5,658,183 | A | 8/1997 | Sandhu et al. |
| 5,672,091 | A | 9/1997 | Takahashi et al. |
| 5,846,373 | A * | 12/1998 | Pirkle et al. ........... 156/345.25 |
| 5,949,927 | A | 9/1999 | Tang |
| 6,024,628 | A | 2/2000 | Chen |
| 6,081,334 | A * | 6/2000 | Grimbergen et al. ....... 356/499 |
| 6,146,248 | A | 11/2000 | Jairath et al. |
| 6,159,073 | A | 12/2000 | Wiswesser et al. |
| 6,172,756 | B1 | 1/2001 | Chalmers et al. |
| 6,207,008 | B1 * | 3/2001 | Kijima ........................ 216/59 |
| 6,261,155 | B1 | 7/2001 | Jairath et al. |
| 6,264,852 | B1 * | 7/2001 | Herchen et al. .............. 216/60 |
| 6,322,714 | B1 * | 11/2001 | Nallan et al. ................. 216/67 |
| 6,358,359 | B1 * | 3/2002 | Peinador et al. ........ 156/345.12 |
| 6,368,182 | B2 * | 4/2002 | Dvir et al. ..................... 451/6 |
| 6,375,540 | B1 | 4/2002 | Mikhaylich et al. |
| 6,447,668 | B1 | 9/2002 | Wang |
| 6,491,569 | B2 | 12/2002 | Bibby, Jr. et al. |

FOREIGN PATENT DOCUMENTS

| | | |
|---|---|---|
| EP | 0 738 561 A1 | 10/1996 |
| JP | 3-234467 | 10/1991 |
| JP | 7-52032 | 2/1995 |
| JP | 9-85611 | 3/1997 |
| WO | WO 95/18353 | 7/1995 |
| WO | WO 98/14306 | 4/1998 |
| WO | WO 00/67951 | 11/2000 |

OTHER PUBLICATIONS

P. Hariharan, "Optical Interferometry,"*Academic Press*, 1985, Orlando, Florida.

J.T. Fanton; Jon Opsal, D.L. Willenborg, S.M. Kelso and Allan Rosencwaig, "Multiparameter measurements of thin films using beam-profile reflectometry,"*J. Applied Physics*, 73(11), Jun. 1, 1993, Fremont, California.

THERMA-WAVE, "Opti-probe 2600," http://www.thermawave.com, 1996, Fremont, California.

J.T. Fanton, Jon Opsal, Allan Rosencwaig and D.L. Willenborg, "A novel technique for performing ellipometric measurements in a sub-micrometer area,"*Therma-Wave, Inc.*, Fremont, California.

THERMA-WAVE, "Opti-Probe,".

T. Bibby, J.A. Adams, and K. Holland, "Optical Endpoint Detection for Chemical Mechanical Planarization,"*Journal of Vacuum Science and tehnology*, B17(5), 2378-2384, 1999.

D.P. Huttenlocher, G.A. Klanderman and W.J. Rucklidge, "Comparing Images Using the Hausdorff Distance,"*IEEE Transactions on pattern Analysis and Machine Intelligence* 15(9), 850-863, 1993.

C.F. Olson, "Maximum-Likelihood Image Matching,"*IEEE Transactions on Pattern Analysis and Machine Intelligence* 24(6), 853-857, 2002.

US 5,306,916, 04/1994, Norton et al. (withdrawn)

* cited by examiner

END POINT DETECTION WITH IMAGING MATCHING IN SEMICONDUCTOR PROCESSING

BACKGROUND OF THE INVENTION

1. Technical Field

The present invention relates generally to semiconductor processing, and more particularly, to end point detection in semiconductor processing using image matching.

2. Related Art

Chemical Mechanical Polishing (CMP) is a well known process for polishing semiconductor wafers. In general, a semiconductor wafer is placed in frictional contact with a moving polishing pad to remove material from the surface of the wafer. The material is typically removed until a desired thickness of the semiconductor wafer is achieved and the polishing process is then terminated. The determination of when to terminate the polishing process is referred to as endpoint detection (EPD).

EPD may take a variety of forms all with the ultimate goal of achieving uniformity among different semiconductor wafers even though process and material variations continuously occur during the polishing process. One category of EPD techniques are known as "in situ" techniques. In situ end point detection operates "on the fly" during the polishing process to measure the semiconductor wafer. The measurement may involve electrical measurement techniques based on capacitance, impedance or conductivity of the wafer. Another measurement technique involves detection of light reflected from the surface of the in-process semiconductor wafer. The reflected light in the form of spectral data is captured and the intensity measured to arrive at an intensity value. The intensity value is indicative of the thickness of the wafer.

A detailed discussion of endpoint detection with a spectral signal is described in international PCT application PCT/US00/12776 published under publication number WO 00/67951. In general, one or more reference semiconductors are polished to a desired thickness and measured to determine a threshold spectral value. During subsequent polishing of other semiconductor wafers, the threshold spectral value is compared with an endpoint signal. For dielectric processing, the endpoint signal is determined from a mathematical model using a spectral value from the semiconductor wafer being polished. For metal polishing, an amplitude ratio that is determined based on division of the amplitude of two pre-selected wavelength bands is used to determine the endpoint signal. When the endpoint signal reaches the threshold spectral value, polishing is terminated.

One drawback to this form of endpoint detection is the significant amount of processing required to translate spectral data to a single value that is an endpoint signal. In addition, due to averaging, ratios and/or other processing of the spectral data to obtain the endpoint signal, accuracy may be compromised. Further, the granularity of repeatable endpoint detection may be undesirably large due to representation of the spectral data with a single value. End point detection based solely on spectral data may also not optimize accuracy in some applications.

SUMMARY

The present invention includes a system for endpoint detection. The endpoint detection system detects one or more desired states of processing of production semiconductor wafers using two-dimensional images. The two-dimensional images utilized by the system include a reference image and a production image.

The reference image may be developed during processing of a reference semiconductor wafer. The reference semiconductor wafer may be part of a wafer group of similar wafers that also includes the production wafer. The reference image may be representative of the desired state of processing. Processing of the reference semiconductor wafer and the production semiconductor wafer may involve for example, chemical mechanical planarization. Accordingly, the desired state of processing may be, for example, a desired wafer thickness.

Following development of the reference image, the production semiconductor may be similarly processed. During processing, a production image may be dynamically developed without interrupting the process. When the dynamically developed reference image and the production image become substantially similar, a process related action may be enabled by the end point detection system, such as enabling termination of the processing of the production semiconductor wafer.

The reference image may be developed by capturing snapshots throughout processing of the reference semiconductor wafer until a desired end point is reached. The snapshots may include process-related data such as spectral information, motor currents, temperatures, etc. From the captured snapshots, a test image may be developed. The test image may be analyzed to determine at least one reference snapshot window representing at least one desired state of processing of the production semiconductor wafer. The reference snapshot window(s) may be used to develop at least one reference image. The reference image may be stored for use by the endpoint detection system during processing of a production semiconductor wafer.

The production image may be developed by sequentially capturing process snapshots during processing of the production semiconductor wafer. The process snapshots may be processed to form the production image. When the production image is determined to be substantially similar to the previously stored reference image, a process related action may be enabled by the endpoint detection system.

An interesting feature of the endpoint detection system involves comparison of the production image to the reference image. The production image may be dynamically updated each time a new process snapshot is captured. The reference image, on the other hand may be developed from a determined number of process snapshots. Accordingly, when the number of process snapshots from which the production image (the production snapshot window) is developed exceeds the number of process snapshots in the reference image (the reference snapshot window), the oldest process snapshot from which the production image is developed drops off to make room for the newest process snapshot. Accordingly, the production image is formed from a moving production snapshot window that is dynamically changed as additional process snapshots are captured.

Another interesting feature of the endpoint detection system also pertains to comparison of the production image to the reference image. Variation between the processing times of the production semiconductor wafers and reference semiconductor wafer(s) may be addressed by dynamically varying the number of process snapshots in the production image. Process related data within the process snapshots may be compressed and expanded to fit within the production snapshot window as the number of process snapshots is dynamically varied. In addition, the size of the reference snapshot window and the production snapshot window may be dynamically varied.

Yet another interesting feature of the endpoint detection system is the process related data captured in the process snapshots that are used to develop the images. One of the process related data variables may be spectral data that is the intensity of light reflected off a surface of the semiconductor wafer being processed. The spectral data may be captured with optical interferometry techniques. Accordingly, a plurality of wavelengths of light intensity over time (t) may be represented in the two-dimensional images. In addition, process related data such as motor current and wafer temperature may also be represented in the images over time (t).

Other systems, methods, features and advantages of the invention will be, or will become, apparent to one with skill in the art upon examination of the following figures and detailed description. It is intended that all such additional systems, methods, features and advantages included within this description, be within the scope of the invention, and be protected by the following claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE PRESENTLY PREFERRED EMBODIMENTS

The present invention includes an endpoint detection system. The endpoint detection system may provide accurate endpoint determination/thickness determination for semiconductor wafer processing. Endpoint determination may be performed with the endpoint detection system by dynamic in-situ capture of process related data. The process related data may be indicative of the current state of processing of a semiconductor wafer. The endpoint detection system may utilize captured and/or generated process related data to develop a production image. During processing the production image may be compared with a reference image to determine a desired state of processing of the production semiconductor wafer, such as endpoint and/or wafer thickness. The endpoint detection system may provide indications and/or control signals when the production image and the reference image are substantially similar.

Figure 1:
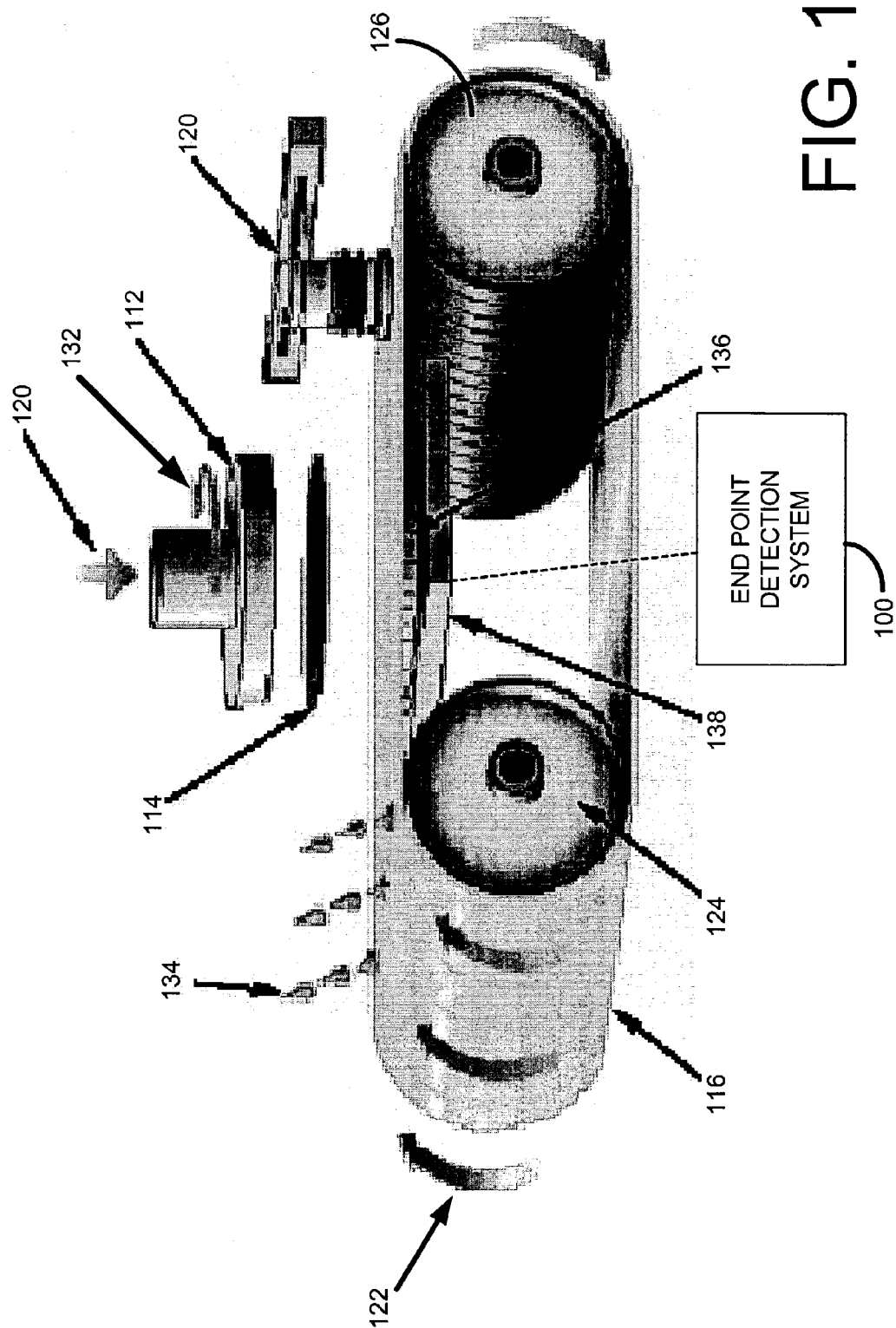
FIG. 1 is a perspective view of an example semiconductor processing machine that includes an endpoint detection system.

FIG. 1 is a perspective view of an example semiconductor processing machine that includes the endpoint detection system 100. The illustrated semiconductor processing machine is a wafer polishing machine that is a linear chemical mechanical planarization (CMP) machine. The wafer polishing machine may be used in interlayer dielectric (ILD) processing, intermetallic dielectric (IMD) processing, pre-metal dielectric (PMD) processing, copper (CU) processing or any other form of planarization processes for semiconductor wafers. The example CMP machine uses linear planarization technology and may be part of a TERES™ Chemical Mechanical Planarization (CMP) system available from Lam Research Corporation located in Fremont, Calif. In other examples any other form of semiconductor processing machine such as Etch, chemical vapor disposition (CVD), etc. that may benefit from endpoint detection or some other desired state of processing may utilize the endpoint detection system 100.

The example semiconductor processing machine also includes a wafer carrier 112 that may have a semiconductor wafer 114 detachably coupled with the wafer carrier 112 by a vacuum or other similar mechanism. The wafer carrier 112 may be maneuvered to place the semiconductor wafer 114 in pressurized contact with a polishing belt 116 as indicated by arrow 120. The polishing belt 116 may represent an endless polishing surface (or pad) that is operable to move horizontally in the direction indicated by arrows 122. The polishing belt 116 may be wrapped around a first roller 124 and a second roller 126. The first or second roller 124 or 126 may be rotated with a roller motor (not shown) at a determined speed.

During polishing, the first and second rollers 124 and 126 may rotate to move the polishing belt 116 linearly against the semiconductor wafer 114 while the wafer carrier 112 may also be rotated as illustrated by arrow 132. A polishing slurry 134 may be added to the polishing belt 116 and a conditioner mechanism 136 may perform reconditioning as the polishing belt 116 moves. The semiconductor wafer 114 may be pressed into the polishing belt 116, while the polishing belt 116 may be supported opposite the semiconductor wafer 114 by an air bearing 136 generated with a platen 138.

Figure 2:
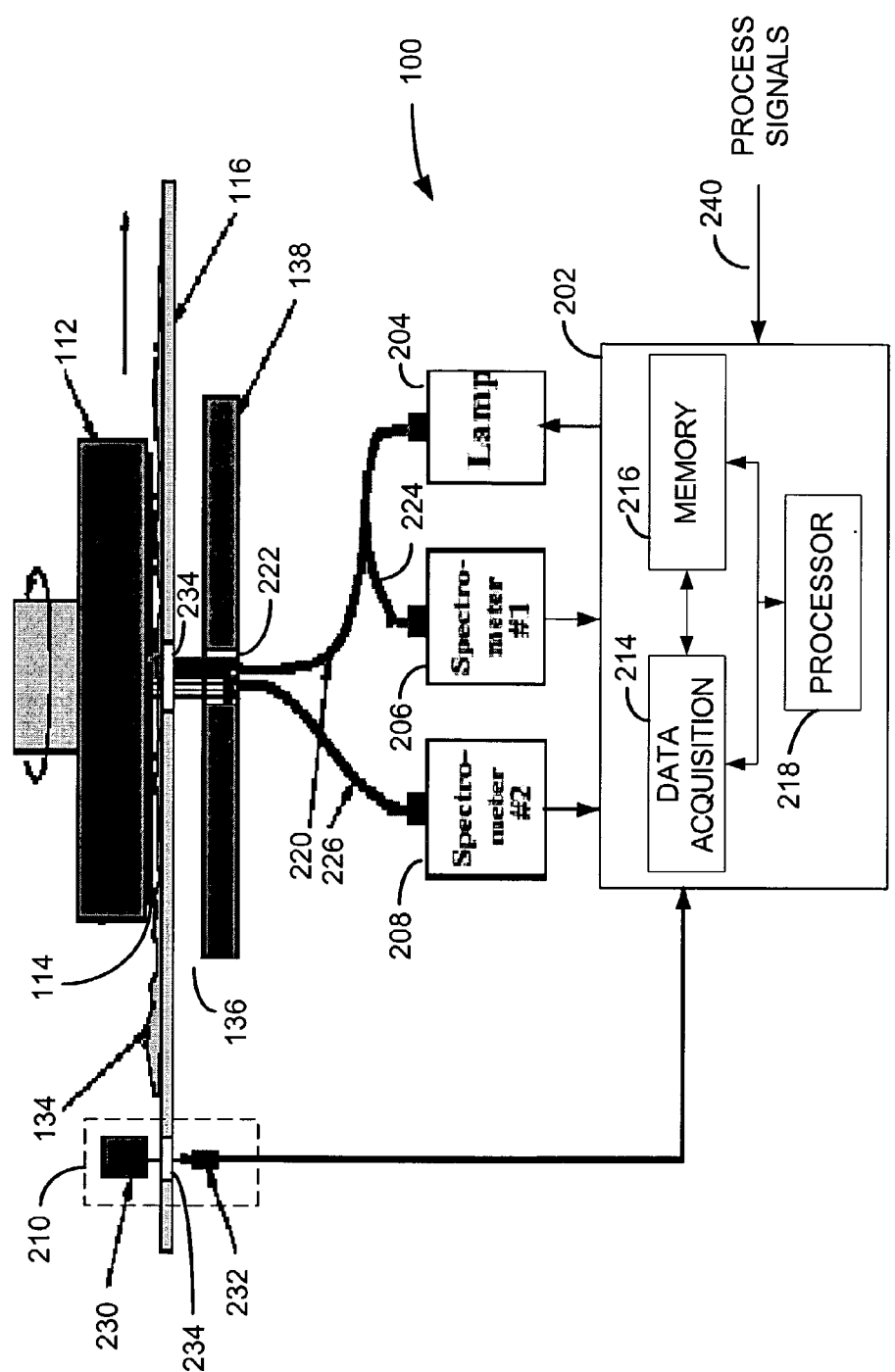
FIG. 2 is a side view of a portion of the semiconductor processing machine and a block diagram of the endpoint detection system of FIG. 1.

FIG. 2 is a more detailed side view a portion of an example semiconductor processing machine and a block diagram of the endpoint detection system 100. As in the previous example, the semiconductor processing machine includes a wafer carrier 112 on which a semiconductor wafer 114 may be detachably mounted. The semiconductor wafer 114 may be positioned in contact with the polishing belt 116. The polishing slurry 134 may be added to the polishing belt 116, and the polishing belt 116 may be supported with the air bearing 136 provided by the platen 138. In other examples, the semiconductor processing machine may include variations and/or different processing features.

The endpoint detection system 100 may be any computer and associated hardware capable of collecting process data related to semiconductor processing that also includes the capture of spectral information. The example endpoint detection system 100 includes a computer 202, a lamp 204, a first spectrometer 206, a second spectrometer 208 and at least one sensor 210. In other examples, fewer or greater numbers of spectrometers, lamps and sensors may be included.

The computer 202 may be any computer-based device(s) capable of executing instructions to control overall operation of the endpoint detection system 100 as a function of inputs to, and outputs from, the endpoint detection system 100. The illustrated computer 202 includes a data acquisition module 214, a memory module 216 and a processor 218. In other examples, greater or fewer numbers of modules may be identified to illustrate the functionality of the computer 202.

The data acquisition module 214 may be any device that provides input/output (I/O) capability for the endpoint detection system 100. The I/O capability may include input and output channels, communication ports, signal conversion, filtering, buffering, wireless communication, wireline communication, optical communication and/or any other I/O related capability. Example signal inputs and outputs include analog signals, digital signals and communication protocols, such as RS422, TCP/IP, etc. The memory module 216 may be any mechanism and/or memory device allowing storage and retrieval of data. For example the memory module 216 may include electronic memory such as flash memory, random access memory (RAM), etc. and/or magnetic memory such as a hard drive(s), an optical disk(s), etc. Data stored in, and accessed from, the memory module 216 may include process related data and operating instructions such as computer code/software for operating the endpoint detection system 100.

The processor 218 may be any computer based device(s) capable of interfacing with the data acquisition module 214 and the memory module 216. Interfacing with the data acquisition module 214 may include receiving indication of one or more input signals and directing the generation of one or more output signals. Interfacing with the memory module 216 may include executing instructions stored in the memory module 216 to generate, store, manipulate and/or extract data within the memory module 216 related to the operation of the endpoint detection system 100. In addition, the processor 218 may coordinate exchanges of data between the data acquisition module 214 and the memory module 216.

The lamp 204 may be any source of radiated light, such as, laser, infrared (IR), incandescent, or any other form of light source. The lamp 204 may be one or more broadband spectral lamps providing light emitted at a predetermined location via an optical fiber. Alternatively, the lamp 204 may be positioned at a predetermined location to directly provide radiated light. In the illustrated example, the light is provided via an optical fiber 220 through a platen aperture 222 in the platen 138. In other examples, other locations/configurations may be utilized for providing the light.

The first and second spectrometers 206 and 208 may be any mechanism or device capable of generating a signal indicative of light intensity. The intensity may be measured in units of foot candles, phots, milliphots, etc. The first and second spectrometers 206 and 208 of the illustrated example may measure the intensity of the light emitted by the lamp 204, and the intensity of the light reflected from the surface of the semiconductor wafer 114, respectively.

The intensity measurement may be performed locally by the first and second spectrometers 206 and 208. Alternatively, the measurement may be performed remotely using optical fibers positioned in predetermined locations. In the illustrated example, the first spectrometer 206 may measure the emitted light intensity of the lamp 204 via a first fiber optic cable 224. The second spectrometer 208 may measure the reflected light intensity of the light being reflected off the surface of the semiconductor wafer 114 via a second fiber optic cable 226 positioned in the platen aperture 222.

The sensor 210 may be any mechanism(s) or device(s) capable of generating a signal indicative of one or more process related data variables associated with processing semiconductor wafers with a semiconductor processing machine. The illustrated example sensor 210 includes a trigger transmitter 230 and a trigger receiver 232 for identifying the location of one or more belt apertures 234 in the moving polishing belt 116.

The lamp 204, the first and second spectrometers 206 and 208 and the sensor 210 may cooperatively operate with optical interferometry techniques to determine process related data in the form of broadband spectral data. As used herein, the term "spectral data" refers to process related data indicative of the intensity of the reflected light energy during a determined time (t) in each of a determined number of wavelengths. For each of the determined wavelengths, the first spectrometer 206 and the second spectrometer 208 may measure light intensity and provide a corresponding signal output.

The sensor 210 may be used to identify when the belt aperture(s) 234 within the moving polishing belt 116 is available to allow light emitting from the lamp 204 to be reflected off the semiconductor wafer 114. In addition, the reflected light intensity (spectral data) may be captured by the second spectrometer 208 based on the information provided by the sensor 210.

The sample time (t) (e.g. timing and capture of light intensity information) may be directed with the computer 202. More specifically, the processor 218 may execute instructions stored in the memory module 216 to direct the data acquisition module 214 to energize the lamp 204 during times when one of the belt apertures 234 is positioned between the lamp 204 and the semiconductor wafer 114. In addition, the processor 218 may execute instructions to capture the reflected light intensity signal from the second spectrometer 208 via the data acquisition module 214.

Other process related data may also be captured by the computer 202. The other process related data may be derived from and/or provided as process signals on at least one process data line 240 to the data acquisition module 214. The process signals may be any information related to processing the semiconductor wafer 114, such as temperatures, voltages, currents, pressures, revolutions-per-minute (RPM), etc. Once captured by the computer 202, the process signals may be associated with the spectral data.

The spectral data and associated other process related data may be collectively referred to as a process snapshot. As used herein, the term "process snapshot" or "process snapshots" refers to associated process related information that is based on data captured by the processor 218 via the data acquisition module 214 during a determined time (t) (e.g. the sample time). In the illustrated example, the time (t) is based on the amount of time one of the belt apertures 234 is positioned between the platen aperture 222 and the semiconductor wafer 114.

Utilizing the process related data, the processor 218 may execute instructions to develop an image. The image may be a two-dimensional image representative of the process-related data from a determined number of process snapshots. The image may represent spectral data from each process snapshot. In addition, the image may also be representative of other process related data provided within each process snapshot.

Figure 3:
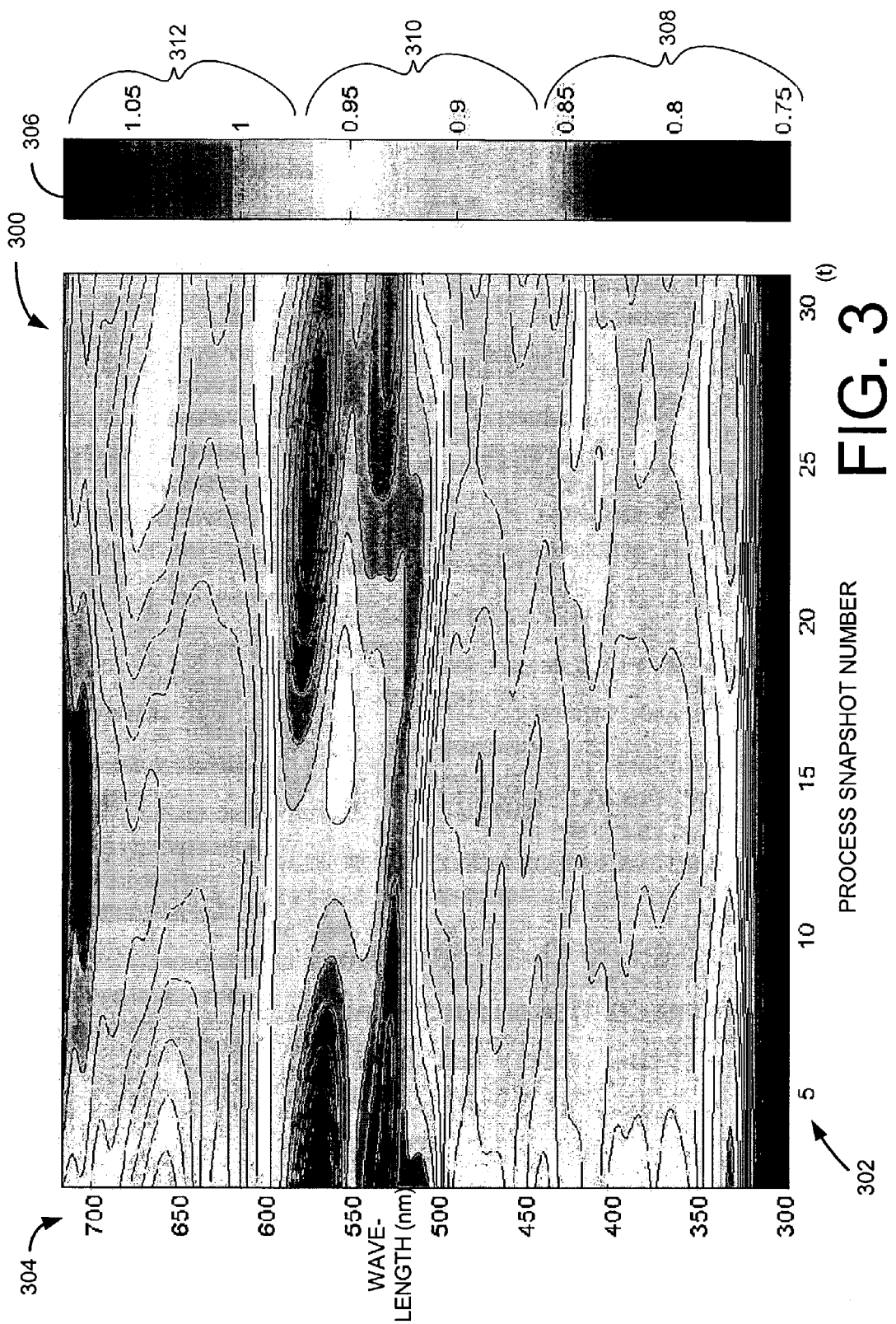
FIG. 3 is an example image developed with the endpoint detection system of FIG. 2.

FIG. 3 is an example two-dimensional image that was developed based on spectral data. The computer 202 may generate an image 300 representative of the spectral data in each wavelength based on normalizing the spectral data. Normalized spectral data may be denoted as $I_{norm}(t;\lambda)$. The normalization may be performed by dividing a reflected light intensity $I_{wafer}(t;\lambda)$ signal generated with the second spectrometer 208 by a lamp intensity $I_{lamp}(t;\lambda)$ of the lamp 204 signal generated with the first spectrometer 206. The result may be further divided by an Si (international standard) reference intensity $I_{Si}(t;\lambda)$ to obtain units of lux per steridian. The Si reference intensity $I_{Si}(t;\lambda)$ utilized is based on the units of the intensity signals generated with the first and second spectrometers 206 and 208. Accordingly, the normalized reflected spectral data may be given by:

$$I_{norm}(t;\lambda) = \frac{\frac{I_{wafer}(t:\lambda)}{I_{lamp}(t:\lambda)}}{I_{Si}(t:\lambda)}. \qquad \text{Equation 1}$$

The normalized spectral data $I_{norm}(t;\lambda)$ may be plotted for each of a plurality of different process snapshots, each captured during a time (t) while a semiconductor wafer 114 is processed. As illustrated in FIG. 3, a plurality of process snapshots 302 may be represented by an image 300. The image 300 may include each of the process snapshots that were captured sequentially over a process time period represented along the x-axis of the image 300. The process time period may be the total of the time (t) from each of the process snapshots 302. The spectral data captured for each of the process snapshots 304 may be in a range of wavelengths ($\lambda$) 304 represented along the y-axis of the image.

In the illustrated example, wavelengths ($\lambda$) 304 in a range of about 300 to 700 nanometers and about thirty process snapshots 302 are utilized to create the image 300. The process snapshots 302 are within a snapshot window that represents the total processing time of the semiconductor wafer. In other examples, other ranges of wavelengths ($\lambda$) 304 and snapshot windows (and therefore number of process snapshots 302) may be selected to form a two-dimensional image.

For example, about thirty process snapshots 302 with spectral data as illustrated may be captured during a process time period within a test image. Following analysis of the test image, a snapshot window may be selected that includes only ten process snapshots 304 and spectral data within a range of wavelengths ($\lambda$) 304 from about 500 nanometers to about 650 nanometers. From the selected snapshot window and the selected wavelengths ($\lambda$) 304, another two-dimensional image including only the selected information may be developed.

In addition to normalization, filtering may also be applied to the spectral data (the reflected light intensity). Filtering may be used to reduce high frequency noise that may be present in the spectral data due to process variations such as vibration, changes in the amount of slurry, etc. The filtering may be any form of filters that reduce process variations such as, two-dimensional low pass filters that are applied in both time (t) and wavelength ($\lambda$) 304 directions to smooth the spectral data in the time axis. Example low pass filters to capture process snapshots are fourth-order Butterworth low-pass filters with cut-off frequency of 0.1 times the highest frequency of signals indicative of the intensity of the reflected light that are generated by the second spectrometer 208.

An intensity of the normalized reflected spectral data $I_{norm}(t;\lambda)$ may be plotted in the determined range of wavelengths ($\lambda$) 304 for each process snapshot 302 to create the image 300. The magnitude of intensity in each of the wavelengths ($\lambda$) 304 for each of the process snapshots 304 may be illustrated in the image 300. For each pixel in the image, a value may correspond to the magnitude of the normalized reflected spectral data. As such, the image may be formed with variable gradients. As illustrated in FIG. 3, a gradient bar 306 identifies intensities that range from a relatively low normalized intensity range 308, through a medium normalized intensity range 310 to a relatively high normalized intensity range 312.

The gradients representative of intensity that are depicted in the image 300 may be color or grayscale. When color gradients are used, for example, shades of blue may be representative of spectral data intensity in the relatively low normalized intensity range 308. Shades of green/yellow may be representative of spectral data intensity in the medium normalized intensity range 310. In addition, shades of orange/red may be representative of intensity in the relatively high normalized intensity range 312. If on the other hand, the intensity in the image 300 is depicted with grayscale gradients, various shades between white and black may be utilized for each of the ranges. In the illustrated grayscale image 300, the gradient bar 306 includes a normalized range from about 0.75 to about 1.05. In other examples, other ranges are possible.

As previously discussed, other process related data included in the process snapshots may also be utilized in creating the image 300. Similar to the spectral data, each of the process related data variables may be represented in the image 300 with gradients. For example if spectral data, roller motor current, and wafer/polishing belt temperature is included in each process snapshot, the spectral data could be represented in the image 300 as previously discussed. The roller motor current and the temperature could be selected to replace one or more selected wavelengths ($\lambda$) 304 on the y-axis of the image 300 within each process snapshot. Similar to the snapshot window and the wavelengths ($\lambda$) 304, the process related data may also be selected to develop another two-dimensional image that includes only the selected information.

One or more gradient bars 306 could be used to identify the range of spectral data, a range of roller motor current, such as, zero to five amperes and a range of temperature such as twenty-five to one hundred degrees Celsius. The particular wavelengths ($\lambda$) 304 that are replaced by other process related data may be at the top or bottom of the y-axis of the image. Alternatively, one or more wavelengths ($\lambda$) 304 anywhere along the y-axis may be replaced; for example where there is little change in intensity of normalized spectral data throughout the process time period.

Referring again to FIGS. 1 and 2, utilizing the endpoint detection system 100, a reference semiconductor wafer (semiconductor wafer 114) may be positioned on the wafer carrier 112. As referred to herein, "a reference semiconductor wafer" is a semiconductor wafer representative of a wafer group of similar production semiconductor wafers. As referred to herein, "production semiconductor wafers" or "a production semiconductor wafer" refers to one or more semiconductor wafers belonging to a group of wafers that are processed through a semiconductor processing machine for polishing, etching, etc.

The wafer group of production semiconductor wafers may be any collection of production semiconductor wafers having one or more similar attributes, characteristics, features or parameters. For example, the wafer group may include production semiconductor wafers produced by a particular semiconductor manufacturer or within a particular manufacturing lot. Alternatively, the reference semiconductor wafer may be representative of a wafer thickness or range of wafer thickness that are similar within a wafer group of production semiconductor wafers.

At least one reference semiconductor may be processed with the semiconductor processing system. During processing, the endpoint detection system 100 may perform in situ capture of process snapshots each of time (t) and develop a test image. The capture of each process snapshot may include the capture of signals representative of spectral data, as well as signals representative of other process related data.

When it is determined that processing of the reference semiconductor wafer reaches a desired state, the test image may be analyzed and a reference snapshot window, a range of wavelengths and a process related variable(s) may be selected to develop a reference image. The reference image may be stored by the processor 218 in the memory module 216. Accordingly, the reference image may be representative of the desired state of processing of the reference semiconductor. Where multiple reference semiconductors are processed to a desired state, each of the test images may be stored and then averaged to arrive at a reference image representative of the desired state.

The desired state may be the point at which processing of the reference semiconductor wafer is complete. In other words, the desired state may be the end point for processing the reference semiconductor. Accordingly, the desired state may be, for example, based on a desired thickness of the semiconductor wafer, a desired translucence of the semiconductor wafer or any other outcome resulting from processing of a semiconductor wafer. Determination of the desired state may be based on visual inspection, measurement, etc. The determination that the desired state has been reached for the reference semiconductor wafer may be made by, for example, intermittently stopping semiconductor wafer processing and performing tests to determine when the desire state has been reached.

Alternatively, the desired state may be one or more determined points within the process time period of the reference semiconductor wafer where actions related to processing are taken. For example, the desired state may be a point in the processing indicating that an additional two minutes of processing remains such that a timer may time out to end the processing. In another example, the desired state may be a point(s) in processing where the consistency/material of the polishing slurry is adjusted, the pressure of the semiconductor wafer on the polishing belt is adjusted, etc.

Following development of the reference image, a production semiconductor wafer from a wafer group represented by the reference semiconductor wafer may be placed on the wafer carrier 112. The production semiconductor wafer may be processed with the semiconductor processing machine. A production image may be dynamically developed by the end point detection system 100. The production image may be developed with process snapshots captured by the end point detection system 100 without interruption of the processing. The capture of process snapshots may include the capture of a signal representative of spectral data, as well as signals representative of other process related data. The process snapshots within a production snapshot window may be used to develop a production image.

The production image may be compared to the stored reference image by instructions executed by the processor 218. When the production image and the reference image are substantially similar, the processor 218 may execute instructions to enable termination of processing of the production semiconductor, adjust the processing, etc. Accordingly, the production semiconductor has reached a desired state of processing, such as a desired thickness.

The production snapshot window of the production semiconductor wafer may include the same number of process snapshots as was included in the reference snapshot window of the reference semiconductor wafer. For example, if the reference image is developed from selected process snapshot numbers ten through nineteen then the reference snapshot window may be fixed at ten process snapshots. A production image developed from process snapshots ten through nineteen may therefore be compared to the reference image.

The production snapshot window used in development of the production image may also be a "moving" production snapshot window. The moving production snapshot window may allow the production image to be dynamically updated with process snapshots captured as processing proceeds. Accordingly, the production snapshot window may include any sequential series of ten process snapshots. For example, process snapshots three through twelve may be used to develop a production image that is compared with a reference image developed based on process snapshots ten through nineteen.

Figure 4:
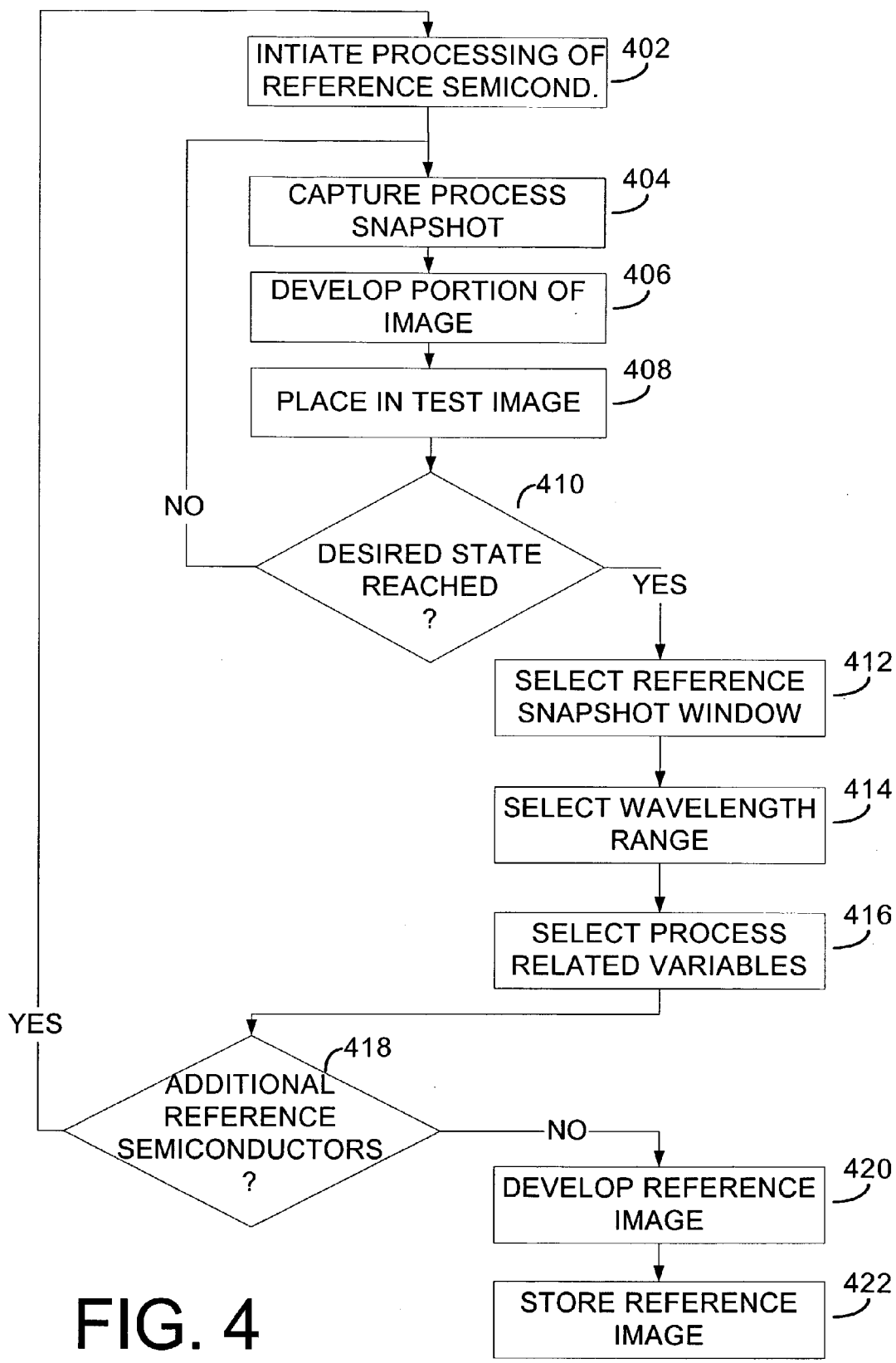
FIG. 4 is a process flow diagram illustrating development of a reference image with the endpoint detection system of FIG. 1.

FIG. 4 is a process flow diagram generally illustrating processing of a reference semiconductor wafer to develop a reference image. The operation begins at block 402, when processing of the reference semiconductor wafer is initiated. At block 404, process related data of the reference semiconductor wafer is captured in a process snapshot during time (t). The process snapshot is processed to develop a portion of an image at block 406. At block 408 the portion of the image is placed sequentially along the x axis of the test image.

It is determined if the desired state of processing of the reference semiconductor wafer has been reached at block 410. If no, processing continues and the operation returns to block 404 to capture another process snapshot. If the desired state of processing has been reached, one or more reference snapshot windows is selected by determining the range of process snapshots that will be used to form a reference image at block 412. At block 414, a range of wavelengths is selected to form the reference image.

Selection of process related data variables to be used in the reference image may be performed at block 416. At block 418, it is determined if there are any additional reference semiconductor wafers to be processed. If yes, the operation returns to block 402 to initiate processing of another reference semiconductor wafer. If there are no additional reference semiconductor wafers to process, the reference image is developed from the selected spectral data, wavelengths and process-related data provided from the reference snapshot windows selected within one or more test images at block 420. At block 422, the reference image is stored.

Figure 5:
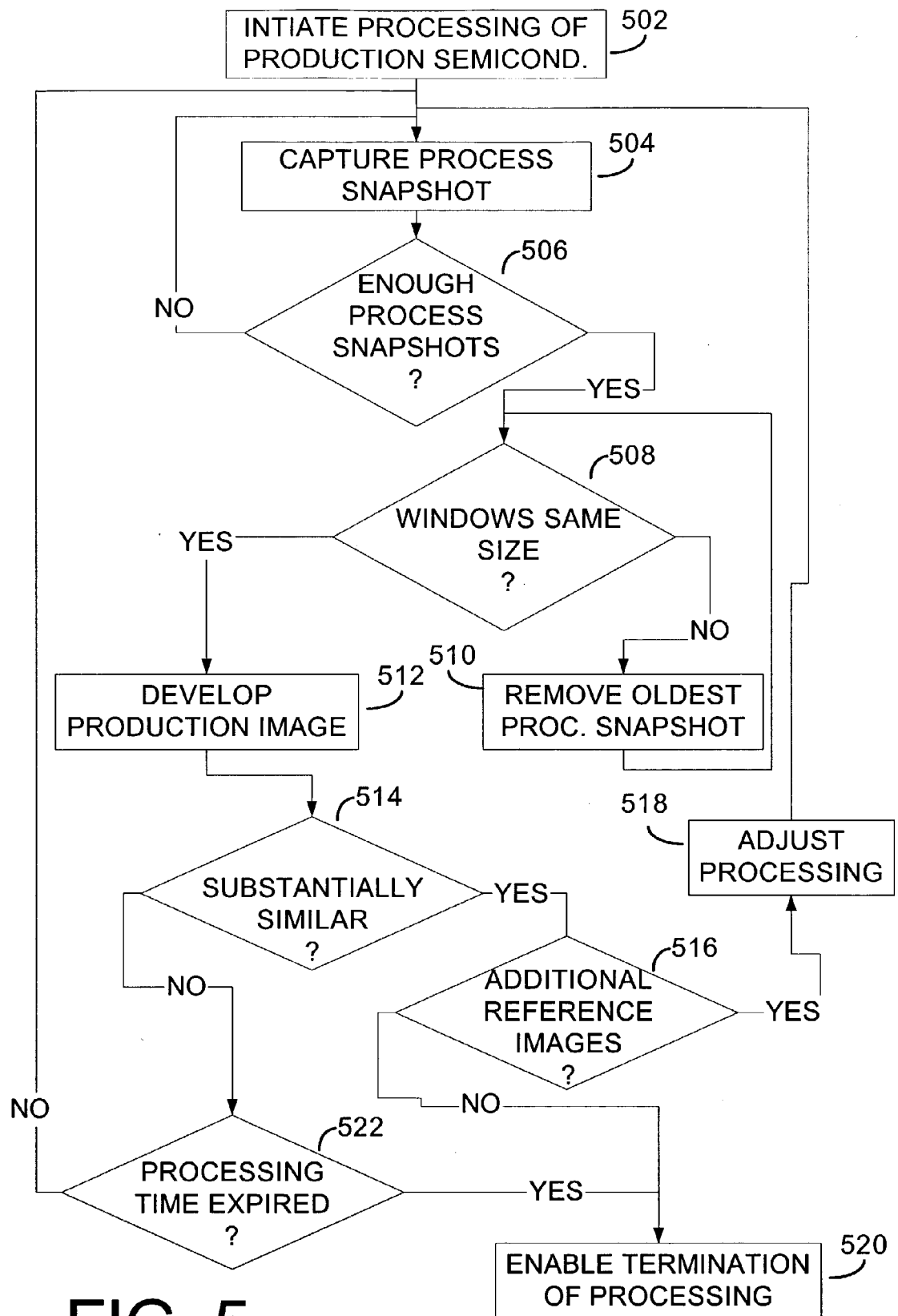
FIG. 5 is a process flow diagram illustrating development of a production image with the endpoint detection system of FIG. 1.

FIG. 5 is a process flow diagram generally illustrating processing of a production semiconductor wafer to perform endpoint determination. The operation begins at block 502, when processing of the production semiconductor wafer is initiated. At block 504, process related data of the production semiconductor wafer is captured in a process snapshot during time (t).

It is determined if there are enough process snapshots to create a production snapshot window that matches the previously developed reference snapshot window used to develop the reference image at block 506. If no, the operation returns to block 504 to capture additional process related data in another process snapshot. If yes, it is determined if the production snapshot window is the same size as the reference snapshot window at block 508. If no, the oldest process snapshot is removed from the production snapshot window at block 510 and the operation returns to block 508.

If the snapshot windows are the same size at block 508, the process snapshot(s) is processed to develop a production image at block 512.

At block 514 the production image is compared with the previously developed reference image. If the production image and the reference image are substantially similar, it is determined if another reference image is to be used during processing at block 516. If yes, processing adjustments are performed at block 518 and the operation returns to block 504 to capture another process snapshot. If no additional reference images are to be used, termination of the processing of the production semiconductor wafer is enabled at block 520. If the production image and the reference image are not substantially similar, it is determined if a determined period of processing time has expired at block 522. If yes, the operation proceeds to block 520 to enable termination of the processing. If the determined period of processing time has not expired, the operation returns to block 504 to capture another process snapshot.

Figure 6:
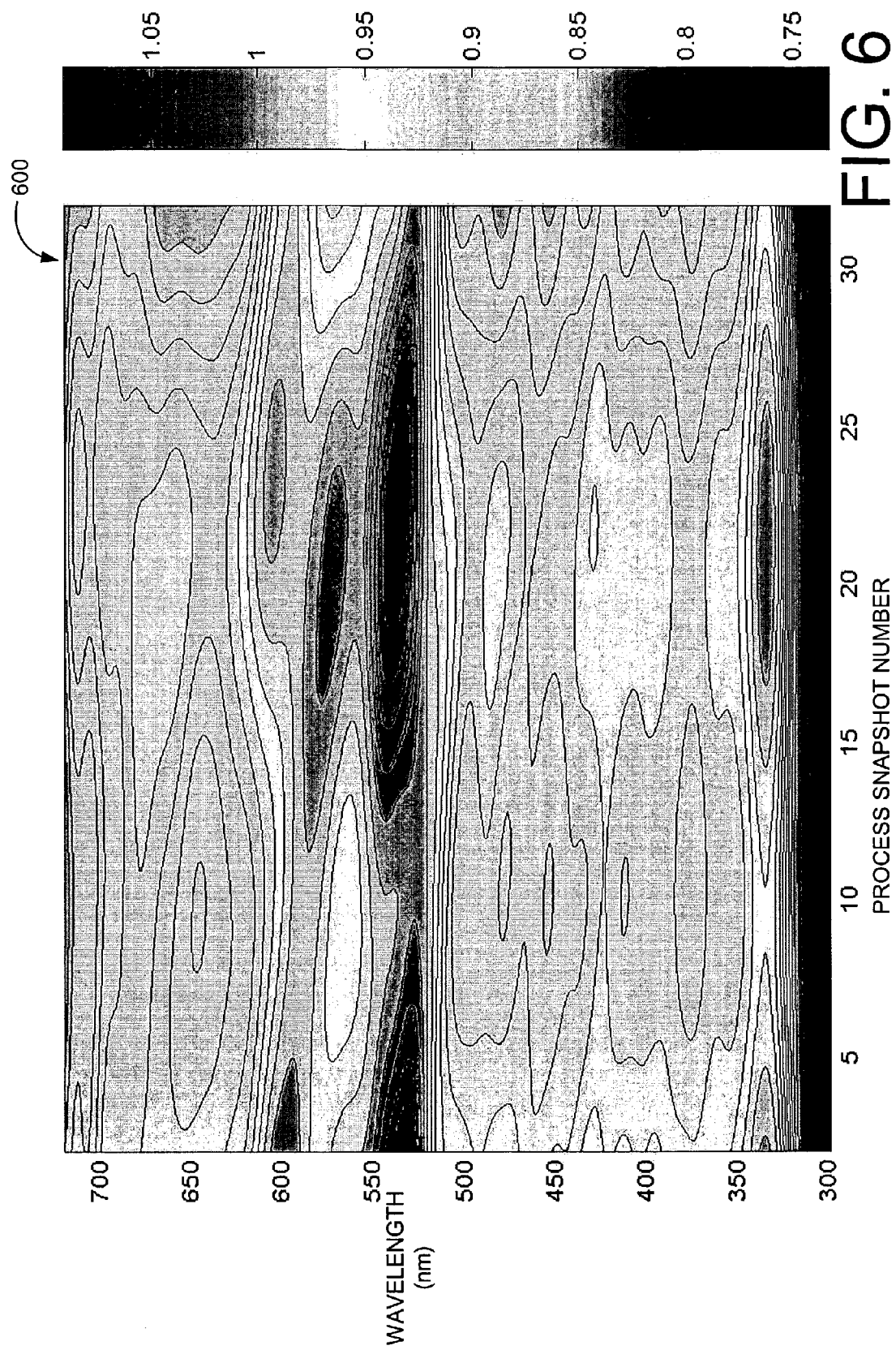
FIG. 6 is an example reference image.
Figure 7:
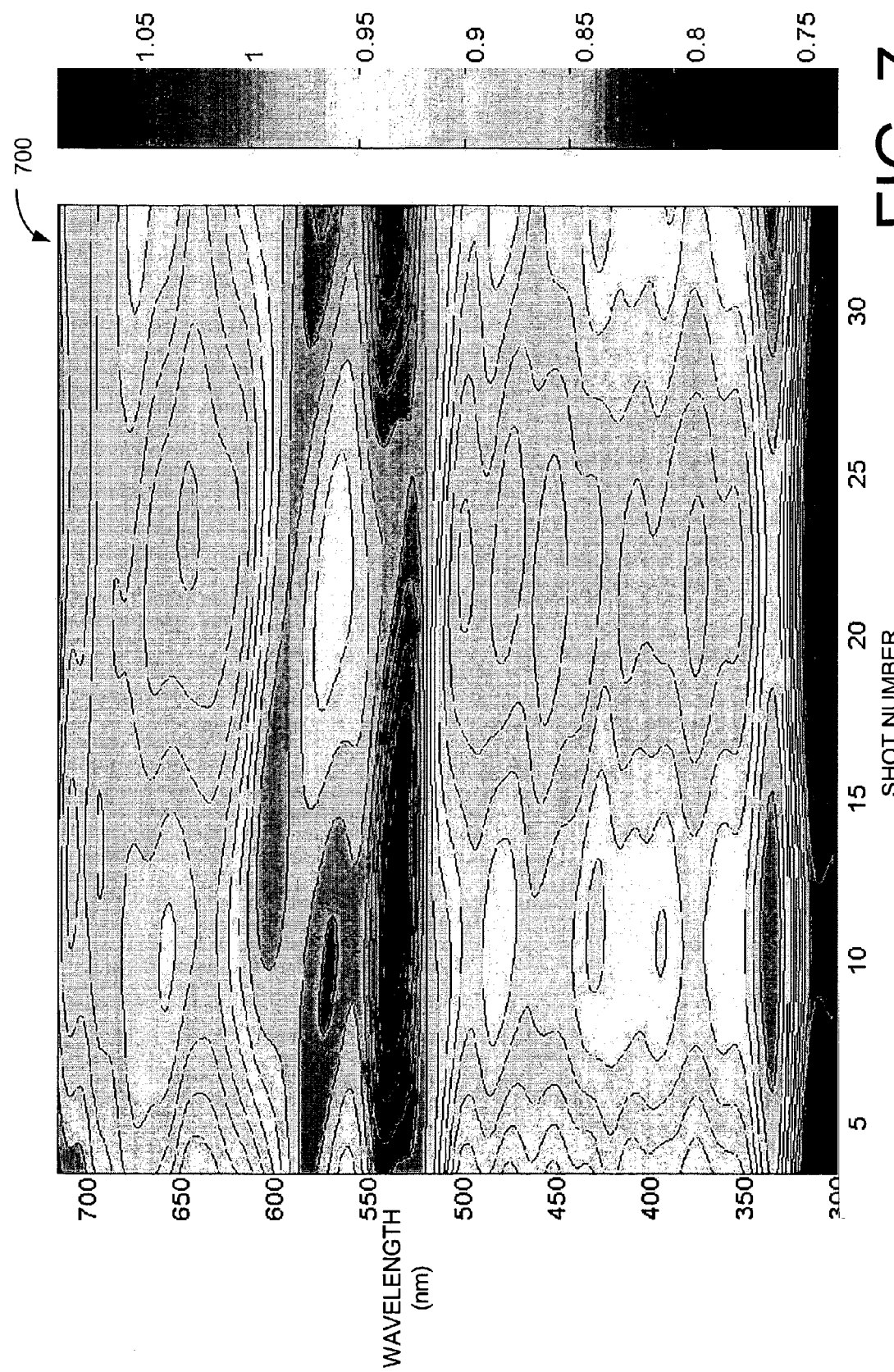
FIG. 7 is an example production image.

Referring now to FIGS. 6 and 7, an example reference image (M) 600 is illustrated in FIG. 6 and an example production image (I) 700 is illustrated is FIG. 7. As illustrated in FIG. 6, the reference image (M) 600 reaches a "valley" around the wavelength of 570 nm for most of the about thirty process snapshots. The valley represents a range of wavelengths with normalized intensity that is relatively low with normalized intensity that is relatively high in both the higher wavelengths (around the 600 nm wavelength) and the lower wavelengths (around the 540 nm wavelength).

The production image (I) 700 of FIG. 7 illustrates an image based on process snapshots captured during processing of a production semiconductor wafer from the wafer group represented by the reference semiconductor wafer. The production image (I) 700 includes a "valley" similar to the "valley" of the reference image (M) 600 illustrated in FIG. 6. Accordingly, the production image (I) 700 may be identified as substantially similar to the reference image (M) 600 and therefore may enable termination or other action related to the processing of the production semiconductor wafer. Substantial similarity of the images may be determined using an image matching technique.

One image matching technique is a sum squares differences (SSD) technique in which the sum of the difference squares provides indication of two-dimensional image matching by:

$$SSD = \sum_i \sum_j (I_{ij} - M_{ij})^2. \quad \text{Equation 2}$$

Where I is the production image, M is the reference image and the terms "i" and "j" are values within a matrix representative of the respective images. Since images are developed with a plurality of pixels, each pixel may represent a value within the matrix. When the production image (I) is substantially similar to the reference image (M), the SSD may reach a minimum value.

Another image matching technique is correlation coefficient (Cor) in which a correlation coefficient may be calculated for the two-dimensional images by:

$$Cor = \frac{\sum_i \sum_j I_{ij} M_{ij}}{\left(\sum_i \sum_j I_{ij}^2 \sum_i \sum_j M_{ij}^2\right)^{\frac{1}{2}}}. \quad \text{Equation 3}$$

Where production image (I) is substantially similar to reference image (M) when Cor is about equal to one. Other possible image matching techniques for determining substantial similarity with a determined level of similarity include a maximum distance (MD) technique, a Hausdorff fraction (HF) technique, a maximum likelihood distance (ML) technique and/or any other technique for determining the similarity between two-dimensional images.

As should be apparent, the endpoint detection system 100 matches an entire two-dimensional production image to an entire two-dimensional reference image. In the case of spectral data, matching may occur across a wide wavelength spectrum that includes three or more wavelengths. In addition, matching may occur with an image developed from a determined number of sequentially collected process snapshots within a snapshot window. As such, significantly more information than a few numerical values is used to maximize the accuracy of detecting when the desired state of processing of a semiconductor wafer is reached.

As previously discussed, the images may include any number of wavelengths and any number of process snapshots. In one example, the reference image is selected to be between wavelengths of 245 pixels (464 nm) and 380 pixels (61 $\mu$m) and snapshot numbers twelve to twenty-one. In this example, the reference image is a 136×10 matrix with a reference snapshot window that includes ten process snapshots. Accordingly, the information within the wavelengths of the production image may be matched to the information of the selected wavelengths of the reference image using the previously discussed image matching techniques.

Substantial similarity may be determined when the intensity within the selected wavelengths meets a determined threshold. The threshold may be fixed or may be variable as a function of process related data variables. One or more different thresholds may be provided based on the number of image matching techniques used to determine substantial similarity. For example, with the images of FIGS. 6 and 7, the calculated values are $Cor_{max}$=7 and the $SSD_{min}$=0.992 therefore a Cor threshold of 10 and an SSD threshold of 0.99 may be selected.

The number of wavelengths and the number of process snapshots used to form an image may also be dynamically varied. Dynamic variation in the number of process snapshots may involve re-scaling of the production image and/or size adjustment of the reference image.

Re-scaling of the production image may include dynamically adjusting the number of process snapshots used in the production snapshot window to develop the production image. In other words, the processing time represented by the production image may be adjusted by re-scaling. Dynamic adjustments in the number of process snapshots may be used to compensate for variations in processing of different production semiconductor wafers. For example, if the removal rate is faster or slower for a production semiconductor wafer, comparison of the same number of process snapshots in the reference image and the production image may not result in substantial similarity due to the differences in processing time. As previously discussed, the process snapshots and therefore the snapshot windows and resulting images are based on the time (t) in which process related data is captured in each process snapshot.

During operation, the number of process snapshots in the production snapshot window may be dynamically varied by a determined amount. The determined amount may be representative of the largest expected variations in processing time between the reference semiconductor wafer and the production semiconductor wafer to reach a desired state(s). For example, a variation of ten percent may be expected and the reference image may have been developed from a reference snapshot window that includes ten process snapshots. As such, the number of process snapshots in the production snapshot window may be dynamically varied between nine and eleven (e.g. +/−ten percent).

Following each dynamic variation, the production image may be developed and compared with the reference image for substantially similarity. Development of the production image may involve compression and expansion of the process snapshots to fill the production snapshot window. For example, process related data within each of eleven process snapshots may be compressed with interpolation techniques to create a production image. Similarly, process related data in nine process snapshots may be expanded with interpolation techniques to create a production image. Alternatively, estimation, prediction or any other data adjustment mechanism may be used to fit the dynamically varying number of process snapshots to the production snapshot window.

The reference image may also be size adjusted during operation. Size adjustment may involve dynamically reducing/increasing the size of the reference image. The size of the reference image may be dynamically varied by using smaller or larger reference snapshot windows, and therefore fewer or greater numbers of process snapshots to develop the reference image. For example, if the reference image was developed from ten process snapshots, then ten process snapshots may be used to develop the production image. If, however, substantial similarity with the reference image actually occurs prior to capturing the first ten process snapshots for the production image, the best opportunity for substantially similar matching may be missed.

With size adjustment, the reference snapshot window may be size adjusted based on the number of process snapshots captured from the production semiconductor wafer. As such, initially, the reference snapshot window may be one snapshot. As more snapshots are captured for the production image, the reference snapshot window may correspondingly be increased in size. Once a determined number of process snapshots have been captured from the production semiconductor wafer, the production snapshot window may be dynamically updated to eliminate the oldest process snapshot and add the latest process snapshot as previously discussed.

Alternatively, the reference snapshot window and the production snapshot window may be dynamically adjusted to compare fewer and greater numbers of process snapshots in an effort to identify substantially similar images. For example, the reference image may be developed based on five process snapshots. Production images developed from five process snapshots of the production semiconductor may then be compared with the reference image.

The number of wavelengths used to develop the reference image and the production image may also be dynamically varied. For example, the image could be developed based on wavelengths of about 450 nanometers to about 650 nanometers where the "valley" was located in FIGS. 6 and 7, or from about 300 nanometers to about 700 nanometers as illustrated. As should be readily apparent, dynamic re-scaling, size adjustment, etc. may also be used alone, sequentially or at the same time to maximize accuracy of determining substantial similarity of the production image and the reference image during processing.

An example test of the accuracy of semiconductor thickness measurements of the endpoint detection system 100 was performed with a chemical mechanical polishing system using ILD pattern wafers. The focus of the test was to validate the accuracy of endpoint detection of a desired state of processing. In this test, the desired state of processing was a desired thickness of the production semiconductor wafers. Within a wafer group of twenty-five test semiconductor wafers, semiconductor wafer number twenty-four was the thickest wafer and was therefore selected as the reference semiconductor wafer. The remaining semiconductor wafers were production semiconductor wafers for purposes of the test.

During polishing to the desired state (e.g. desired wafer thickness) of the reference semiconductor wafer, thirty-two snapshots were captured and a representative test image was developed. Following analysis, the reference image was developed from a reference snapshot window the included process snapshot numbers twenty through twenty-nine. The thickness of the reference semiconductor wafer was estimated at process snapshot number twenty-nine as about:

$$d_{24}(29) = d_{24}(t_{post}) + RRF \times (t_{post} - t_{29}). \qquad \text{Equation 4}$$

Where $d_{24}$ is the estimated thickness, RRF is a removal rate factor that is estimated at process snapshot number 29 as described later, $t_{post}$ is the process time period (total processing time) and $t_{29}$ is the time(t) during which process snapshot number 29 was captured.

In the example test image, the reference snapshot window was chosen to include process snapshots twenty one through twenty nine since some of the production semiconductor wafers in the wafer group were thinner after polishing, and therefore may have shorter polishing times to reach the desired state. Estimation of the removal rate (RR) may be based on the difference of the pre-thickness measurement and the post-thickness measurement divided by the recorded process time period $t_{post}$ of the reference semiconductor wafer. In the example test, a factor of 0.45 was used for the removal rate factor (RRF) of the reference semiconductor wafer at process snapshot number 29.

A scaling factor $S_{RR}$ may be chosen when the best image matching is reached. For this example, a reference snapshot window of ten process snapshots and a range of 0.9–1.3 re-scaling (e.g. −10 percent to +30 percent processing variations) was utilized during processing of the reference semiconductor wafer. The estimate of thickness may be based on the best substantial similarity of the production image and the reference image.

The following table provides thickness estimates based on processing each of the production semiconductor wafers until substantially similarity of the reference image and the production image was identified. Semiconductor wafer number twenty-four (the reference semiconductor wafer) was estimated with a thickness $d_r$ of 11442 Angstroms and an estimated removal rate of RR=3073 Angstroms/min.

|  | #1 | #2 | #3 | #4 | #5 | #6 | #7 | #8 | #9 | #10 | #11 | #12 |
|---|---|---|---|---|---|---|---|---|---|---|---|---|
| $d_i$ (Å) | 11642 | 11821 | 11697 | 11751 | 11742 | 11680 | 11649 | 11657 | 11665 | 11874 | 11617 | 11649 |
| $\Delta d$ (Å) | 201 | 379 | 256 | 309 | 300 | 239 | 207 | 216 | 224 | 433 | 175 | 207 |
| $Cor_{max}$ (Å) | 0.938 | 0.999 | 0.991 | 0.993 | 0.989 | 0.999 | 0.998 | 0.995 | 0.973 | 0.996 | 0.999 | 0.982 |
| RR (Å/min) | 3250 | 3063 | 3141 | 3068 | 3092 | 3106 | 3082 | 2997 | 3149 | 3013 | 3066 | 3021 |
| $S_{RR}$ | 1.08 | 0.96 | 1.01 | 0.91 | 0.91 | 1.01 | 1.02 | 1.05 | 0.91 | 0.91 | 1.02 | 0.91 |
|  | #13 | #14 | #15 | #16 | #17 | #18 | #19 | #20 | #21 | #22 | #23 | #25 |
| $d_i$ (Å) | 11726 | 11706 | 11506 | 11789 | 11679 | 11892 | 11571 | 11848 | 11887 | 11814 | 11457 | 11675 |
| $\Delta d$ (Å) | 284 | 264 | 64 | 347 | 237 | 450 | 129 | 405 | 445 | 372 | 15 | 233 |
| $Cor_{max}$ (Å) | 0.985 | 0.995 | 0.985 | 0.999 | 0.949 | 0.991 | 0.998 | 0.995 | 0.998 | 0.989 | 1 | 0.977 |
| RR (Å/min) | 3071 | 3008 | 3062 | 2922 | 3051 | 2999 | 2994 | 2957 | 2975 | 2953 | 3013 | 3109 |
| $S_{RR}$ | 0.91 | 1.06 | 1.1 | 1.04 | 1.02 | 1.07 | 1.07 | 1.03 | 0.91 | 0.96 | 1.08 | 1.02 |

The estimate of thickness is based on the "best" matching process snapshot with the reference image from semiconductor wafer number twenty-four. As can be seen, there are some relatively large thickness estimate errors (Δd). In reviewing the correlation it was found that most production semiconductor wafers have high correlation coefficients (Cor).

There appeared to be little significant relationship between maximum correlation coefficients and the estimate thickness errors. It can be seen that the proposed image matching algorithms work well with the estimate of the film thickness. Furthermore, considering the production semiconductor wafers with maximum estimated thickness errors (Δd) that were more than 350 Angstroms, i.e. semiconductor wafer numbers 2, 10, 16, 18, 20, 21 and 22, these errors may have resulted from estimating errors in the estimated removal rate factor (RRF) due to variations in removal rate.

In the above calculations, the removal rate factor (RRF) of 0.45 was used to estimate the removal rate (RR) from the pre- to the post-thickness measurement. At the beginning of CMP processing, the surface of the semiconductor wafer is not planarized and topological differences in the surface exist due to the deposition films. As such, the removal rate (RR) near the beginning of processing may be higher than the removal rate (RR) when the surface of the wafer becomes more planarized later in the period of processing. To account for the slower removal rate (RR) near the end of processing (such as at process snapshot number 29), the removal rate factor (RRF) may be used.

Since the removal rate may decrease at an unknown rate for the ILD pattern wafers used in the test, and the process snapshot number used for the reference image is close to the end of the process time period, the estimated removal rate factor (RRF) may be varied in order to check for large variations in the estimated thickness errors (Δd). In additional tests where the removal rate factor (RRF) was varied to be about 0.6 or 0.7, the maximum estimated thickness errors increased.

Figure 8:
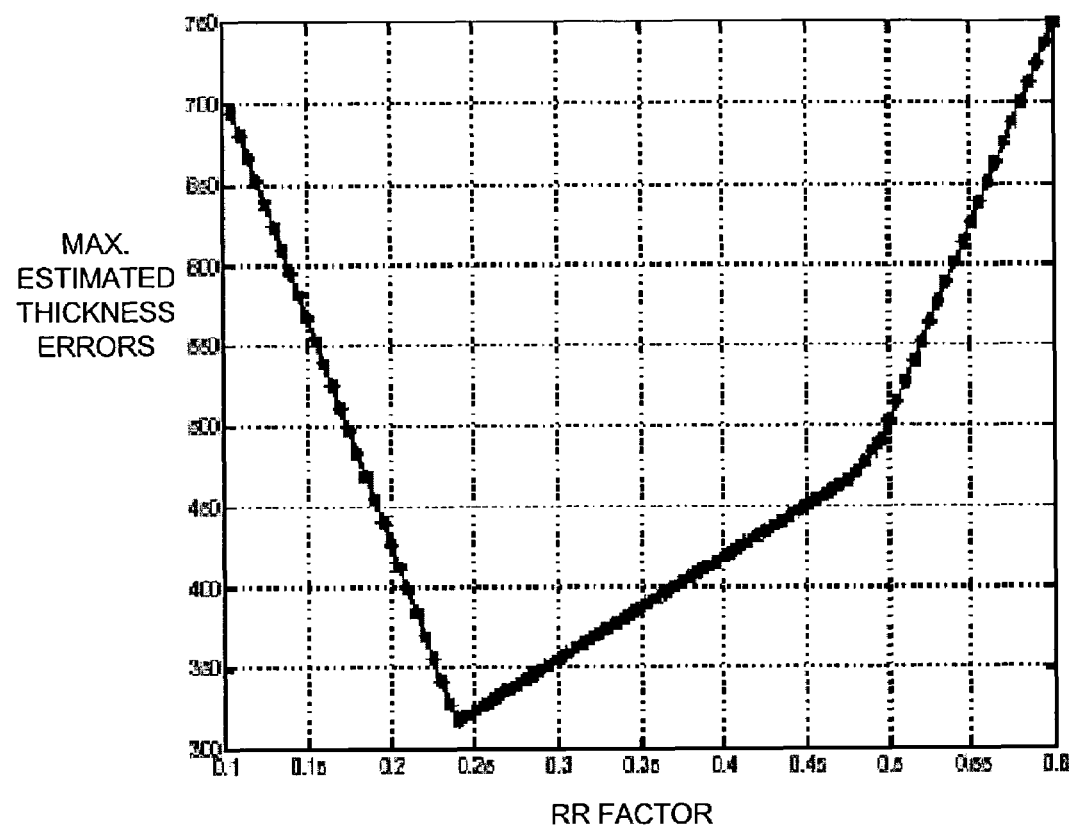
FIG. 8 is example test results based on operation of the endpoint detection system of FIG. 1.

The relationship between maximum estimated thickness errors and the removal rate factor is illustrated in FIG. 8. As illustrated in FIG. 8, when the removal rate factor (RRF) is about 0.25, the maximum estimated thickness errors (Δd) reach minimum values. A more realistic value of the removal rate factor (RRF) in the previously described test was around 0.45–0.5, which corresponds to a removal rate (RR) of about 3000 Angstroms/min to about 4000 Angstroms/min. Around these values, the maximum estimated thickness error values (Δd) may be around 450–550 Angstroms.

The previously discussed end point detection system 100 may be used to accurately determine a desired state of processing of production semiconductor wafers utilizing in situ measurement techniques. The desired state may be determined based on comparison of a reference image with a production image developed during processing of a production semiconductor wafer. The reference image may be previously developed based on processing of a reference semiconductor wafer to the desired state of the production semiconductor wafer. The images may be representative of spectral data captured with optical interferometry techniques. In addition, the images may be representative of other process related data. When the comparison indicates substantial similarity between the reference and production images, actions related to the process such as enabling termination of processing may occur.

While the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A method of detection of a desired state of processing of a semiconductor wafer, the method comprising:
   forming a process snapshot with captured spectral data representative of light intensity in a plurality of wavelengths;
   sequentially collecting process snapshots while processing a production semiconductor wafer;
   processing a plurality of process snapshots to form a production image;
   comparing all of the wavelengths of the production image to a reference image having a plurality of wavelengths; and
   signaling when the light intensity of the wavelengths of the production image and a light intensity of the wavelengths of the reference image are within a determined level of similarity.

2. The method of claim 1, wherein processing comprises representing spectral data and other process related data with the production image.

3. The method of claim 1, wherein processing comprises dynamically re-scaling the production image to compensate for variation in processing of the semiconductor wafer by adjustment of the number of wavelengths included in the production image.

4. The method of claim 1, wherein spectral data is captured utilizing optical interferometry.

5. The method of claim 1, wherein comparing comprises performing image matching techniques to determine substantial similarity between the production image and the reference image.

6. The method of claim 1, wherein signaling comprises enabling termination of the processing of the production semiconductor wafer.

7. The method of claim 1, wherein processing a plurality of process snapshots comprises forming the production image from a plurality of variable gradients that are at least one of color gradients or grayscale gradients or combinations thereof, wherein at least a portion of the variable gradients are representative of spectral data from each of the process snapshots.

8. The method of claim 1, wherein comparing all of the wavelengths of the production image comprises size adjusting the reference image based on the number of snapshots used to form the production image.

9. A method of detection of a desired state of processing of a semiconductor, the method comprising:
processing a reference semiconductor to a desired state;
capturing process related data indicative of the desired state in the form of a two-dimensional reference image;
representing light intensity in each of a plurality of wavelengths in the two-dimensional reference image, wherein the level of the light intensity in each of the wavelengths is resented with corresponding color from a predefined range of colors;
processing a production semiconductor after the reference semiconductor;
capturing process related data indicative of the current state of the production semiconductor in the form of a two-dimensional production image;
representing light intensity in each of a plural of wavelengths in the two-dimensional production image, wherein the level of light intensity in each of the wavelength is represented with corresponding color from the predefined range of colors; and
signaling when the color present in the two-dimensional production image and the color present in the two-dimensional reference image are substantially similar.

10. The method of claim 9, wherein processing comprises chemical mechanical planarization of the reference semiconductor and the production semiconductor.

11. The method of claim 9, wherein capturing process related data indicative of the desired state in the form of a two-dimensional production image comprises:
sequentially collecting process snapshots to develop the two-dimensional production image; and
eliminating an oldest process snapshot in favor of a newest process snapshot to keep a production snapshot window from exceeding the size of a reference snapshot window.

12. The method of claim 9, wherein capturing process related data indicative of the desired state in the form of a two-dimensional production image comprises adjusting the size of the reference image as a function of the size of the production image.

13. The method of claim 9, wherein capturing process related data indicative of the desired state in the form of a two-dimensional production image comprises re-scaling the production image by dynamic adjustment of the quantity of process snapshots used to develop the production image.

14. The method of claim 9, wherein capturing process related data indicative of the desired state in the form of a two-dimensional production image comprises selecting a range of process snapshots for the production image that are other than a range of process snapshots used to form the reference image.

15. The method of claim 9, wherein capturing process related data indicative of the desired state in the form of a two-dimensional production image comprises adjusting the number of wavelengths represented in the reference image and the production image.

16. The method of claim 9, wherein capturing process related data comprises capturing spectral data, a roller motor current and a semiconductor wafer temperature in each of a plurality of process snapshots.

17. An endpoint detection system for detection of a desired state of processing, the endpoint detection system comprising:
a memory device;
instructions stored in the memory device to dynamically develop a two-dimensional production image that displays variations in the magnitude of process related data with corresponding colors from a predefined range of colors as a function of ongoing processing of a production semiconductor wafer;
instructions stored in the memory device to compare the two-dimensional production image to a two-dimensional reference image that also displays variation in the magnitude of the process related data with corresponding colors from the predetermined range of colors, wherein the two-dimensional reference image is representative of a desired state of processing of the two-dimensional production image; and
instructions stored in the memory device to generate a signal when the colors present in the two-dimensional production image and the colors present in the two-dimensional reference image are substantially similar.

18. The endpoint detection system of claim 17, wherein the instructions stored in the memory device to dynamically develop the two-dimensional production image comprise instructions to capture a process snapshot that includes spectral data indicative of the intensity of light in a plurality of wavelengths that is reflected off a surface of the production semiconductor wafer.

19. The endpoint detection system of claim 17, wherein the instructions stored in the memory device to dynamically develop the two-dimensional production image comprise instructions to represent spectral data from a plurality of wavelengths and other process related data in the two-dimensional production image.

20. The endpoint detection system of claim 17, wherein the instructions to dynamically develop a two-dimensional production image comprise instructions stored in the memory device to add a new process snapshot and removing an oldest process snapshot to enable a movable production snapshot window.

21. The endpoint detection system of claim 17, wherein the instructions to dynamically develop a two-dimensional production image comprise instructions stored in the memory device to re-scale the production image by adjustment of the processing time represented in the production image.

22. An endpoint detection system for detection of a desired state of processing, the endpoint detection system comprising:
a computer,
a first signal provided to the computer, wherein the first signal is representative of the desired state of processing of a reference semiconductor wafer with data indicative of the intensity of light in each of a plurality of wavelengths, wherein the computer is operable to develop a reference image as a function of the first signal, the reference image is developed to display the intensity of light in each of the wavelengths with a corresponding color from a predetermined range of colors; and a second signal dynamically provided to the computer during processing of a production semiconductor wafer, wherein the second signal is representative of the state of processing of the production semiconductor wafer with data indicative of the intensity of light in each of a plurality of wavelengths, wherein the computer is operable to develop a production image as a function of the second signal, the production image is developed to display the intensity of light in each of the wavelengths with a corresponding color from the predetermined range of colors, wherein the computer is operable to compare the reference image and the production image and provide a third signal when the reference image and the production image are substantially similar.

23. The endpoint detection system of claim 22, wherein the first and second signals are spectral data representative of the intensity of light reflected off the surface of a semiconductor wafer.

24. The endpoint detection system of claim 22, wherein the computer comprises a data acquisition module, a memory module and a processor.

25. The endpoint detection system of claim 22, wherein the reference image and the production image are developed from a plurality of process snapshots that are captured as a function of the respective first and second signals during processing of the reference semiconductor wafer and the production semiconductor wafer, respectively.

26. A method of detection of a desired state of processing of a semiconductor wafer, the method comprising:

simultaneously capturing the intensity of a plurality of wavelengths of light energy in each of a plurality of sequentially collected snapshot images;

developing a production image that represents the intensity of the light energy in the wavelengths of the snapshot images with at least one of color gradients or gray scale gradients or combinations thereof; and comparing the at least one of color gradients or gray scale gradients or combination thereof that are included in the production image with at least one of color gradients or gray scale gradients, or combinations thereof that are included in a reference image.

27. The method of claim 26, wherein comparing the at least one of color gradients or gray scale gradients comprises image matching the production image and the reference image to be substantially similar above a determined threshold.

28. The method of claim 26, wherein developing a production image comprises representing other process related variable data with at least one of color gradients or gray scale gradients in the production image.

29. The method of claim 28, wherein representing other process related data comprises plotting at least one of a roller motor current or a semiconductor wafer temperature.

30. The method of claim 26, wherein comparing the at least one of color gradients or gray scale gradients comprises adjusting the size of the reference image as a function of the number of process snapshots used to plot the production image.

31. The method of claim 26, wherein developing a production image comprises re-scaling the production image by dynamic adjustment of the quantity of process snapshots used to develop the production image.

32. The method of claim 26, wherein developing a production image comprises selecting a range of process snapshots for the production image that are other than a age of process snapshots used to form a reference image.

* * * * *

UNITED STATES PATENT AND TRADEMARK OFFICE
CERTIFICATE OF CORRECTION

PATENT NO. : 6,930,782 B1  Page 1 of 1
DATED : August 16, 2005
INVENTOR(S) : Jingang Yi et al.

It is certified that error appears in the above-identified patent and that said Letters Patent is hereby corrected as shown below:

Column 17,
Line 29, change "resented" to -- represented --.
Line 36, change "plural" to -- plurality --.

Column 20,
Line 38, change "age" to -- range --.

Signed and Sealed this

First Day of November, 2005

JON W. DUDAS
*Director of the United States Patent and Trademark Office*